United States Patent
Anderson

(10) Patent No.: US 7,701,332 B2
(45) Date of Patent: Apr. 20, 2010

(54) REMOTE DEVICE FOR A MONITORING SYSTEM

(75) Inventor: David T. Anderson, Hamburg, MN (US)

(73) Assignee: Healthsense, Mendota Heights, MN (US)

(*) Notice: Subject to any disclaimer, the term of this patent is extended or adjusted under 35 U.S.C. 154(b) by 498 days.

(21) Appl. No.: 11/488,963

(22) Filed: Jul. 19, 2006

(65) Prior Publication Data

US 2007/0152811 A1    Jul. 5, 2007

Related U.S. Application Data

(63) Continuation-in-part of application No. 11/323,077, filed on Dec. 30, 2005.

(51) Int. Cl.
*G08B 1/08* (2006.01)

(52) U.S. Cl. ............ 340/539.11; 340/506; 340/539.1; 340/825.36; 340/825.49

(58) Field of Classification Search .......... 340/506, 340/539.1, 539.13, 825.36, 825.49
See application file for complete search history.

(56) References Cited

U.S. PATENT DOCUMENTS

| 5,400,246 A | * | 3/1995 | Wilson et al. .......... 700/17 |
| 6,542,076 B1 | * | 4/2003 | Joao ................. 340/539.14 |

FOREIGN PATENT DOCUMENTS

| EP | 1 571 583 | 9/2005 |
| EP | 1 585 077 | 10/2005 |

* cited by examiner

*Primary Examiner*—Daryl Pope
(74) *Attorney, Agent, or Firm*—Brooks, Cameron & Huebsch, PLLC

(57) ABSTRACT

Embodiments of the present invention relate to methods, devices, and systems to monitor activity. One system to monitor activity includes a remote device including a home/away sensor and a transmitter. The embodiment also includes a local interface that receives a wireless signal from the transmitter and a base station operably coupled to the local interface. The base station can include a receiver for receiving signals from a number of sensors and a logic component that institutes rules to determine whether to initiate an alert based on one or more activations of the home/away sensor.

34 Claims, 4 Drawing Sheets

US 7,701,332 B2

REMOTE DEVICE FOR A MONITORING SYSTEM

CROSS-REFERENCE TO RELATED APPLICATIONS

This application is a continuation-in-part of U.S. application Ser. No. 11/323,077, filed Dec. 30, 2005.

BACKGROUND OF THE DISCLOSURE

Methods, devices, and systems have been developed in various fields of technology for the monitoring of the movement and/or health of an individual. In the field of remote health monitoring, for instance, systems have been developed to enable an individual to contact medical professionals from their dwelling regarding a medical emergency.

For example, in various systems, a system is equipped with an emergency call button on a base station that initiates a call or signal to an emergency call center from a user's home telephone. The concept of such a system is that if an individual has a health related problem, they can press the emergency call button and emergency medical providers will respond to assist them.

To aid in situations, such as where an individual has fallen and cannot reach an emergency call button on the base station, portable devices have been developed. The portable devices generally include an emergency call button that transmits a signal to the base station in the dwelling indicating an emergency. Once the signal is made, the base station alerts a remote assistance center that can contact emergency medical personnel or a designated third party. Such devices are typically usable only within the dwelling of the individual and within a short distance to the base station.

Systems have also been developed that use sensors within the home to monitor an individual within a dwelling. Typically, these systems include motion sensors, for example, that are connected to a base control system that monitors areas within the dwelling for movement. When a lack of movement is indicated, the system indicates the lack of movement to a remote assistance center that can contact a party to aid the individual.

However, not all inactivity indicates that an individual is in need of assistance. For example, an individual can be sitting in a chair for a prolonged period, or lying in bed. These periods may be sufficient to initiate an alert for third party response, but may not actually be an emergency. In some of these systems, the system is designed to allow a third party to intervene to aid the individual according to the analysis of the information received by the remote assistance center.

Further, emergency call button devices and systems that use a number of sensors to monitor an individual and do analysis on the information collected typically use the call button or a sensor of the sensing system in isolation. Additionally, such sensing systems also monitor the health of the system, and its sensors, based upon the individual sensor activations. That is, a sensor can be activated, but may not be correlated with any other sensors in the system. Accordingly, the certainties of the sensor activations of these systems and/or the determinations of whether to take an action by a system are based upon the reliability and reception of signals from individual sensors.

DETAILED DESCRIPTION OF THE DISCLOSURE

Figure 1:
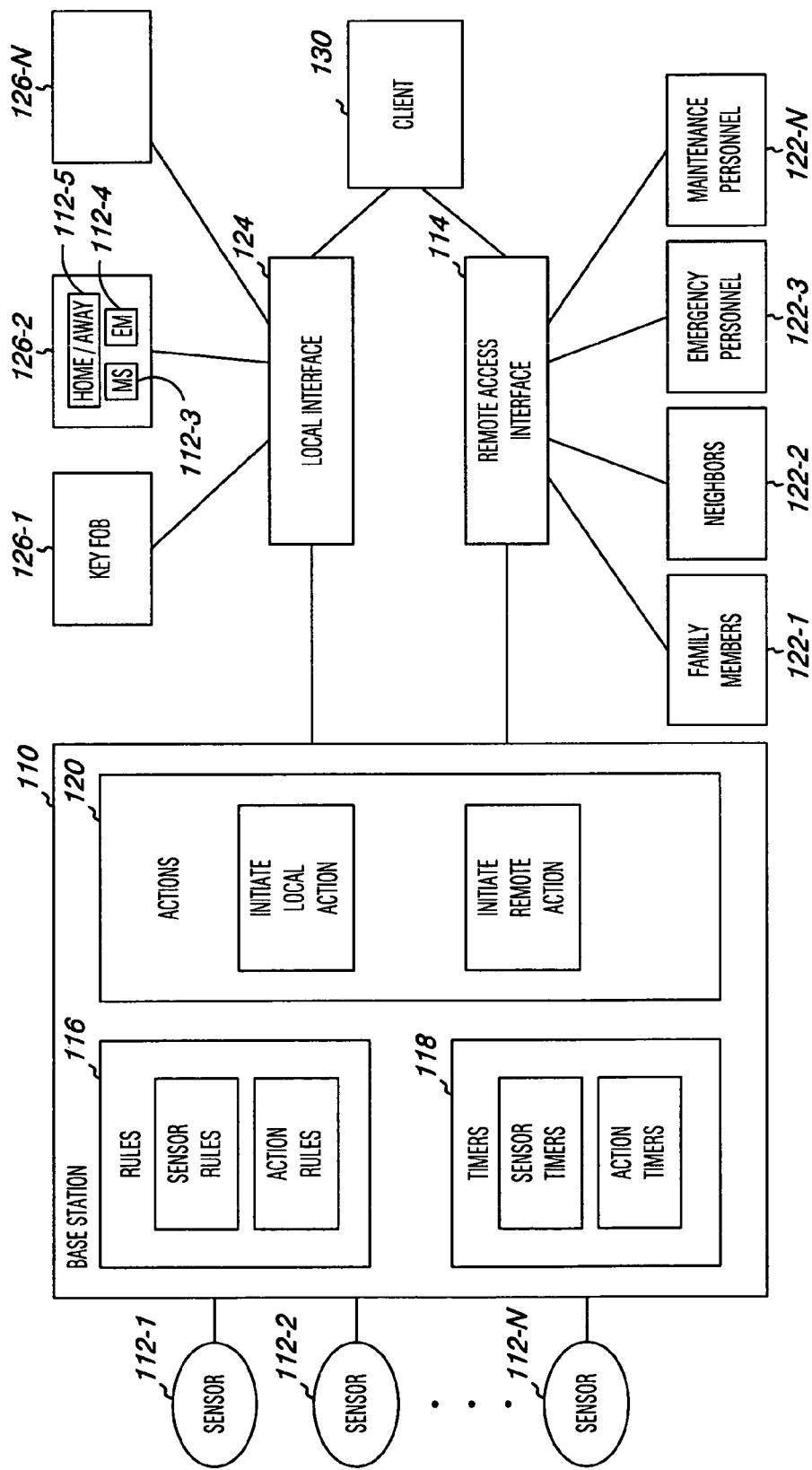
FIG. 1 illustrates a monitoring system embodiment.

Embodiments of the present disclosure can provide simple, cost effective, privacy-respecting, and relatively non-intrusive methods, devices, and systems for monitoring activity. Embodiments of the present disclosure, for example, can be utilized with and can include systems and devices as described in U.S. application Ser. No. 11/323,077, filed Dec. 30, 2005. The present disclosure provides detail into remote device concepts that can be used with the systems discussed in the above referenced application, the present application, and/or other systems for monitoring one or more individuals.

For instance, embodiments can include systems to monitor the activity of an individual within a dwelling and to monitor whether the individual is absent from a dwelling or a surrounding area. As used herein, a "dwelling" can be a house, condominium, townhouse, apartment, or institution (e.g., hospital, assisted living facility, nursing home, prison, etc.).

To monitor the activity of an individual, various systems can provide automated detection of changes in activity within a dwelling and automated initiation of alerts to third parties to check on and/or assist the individual where assistance is needed, thereby avoiding prolonged periods of time before assistance is provided. Some systems can utilize multiple sensors, multiple timers, and/or multiple rules to determine whether to initiate an action, thereby increasing the certainty that an action is necessary and should be initiated. Various systems also can utilize multiple sensors, multiple timers, and/or multiple rules to make statistical correlations between a number of sensors, thereby increasing certainty that the system is in satisfactory health.

Embodiments can also include a home/away sensor and a transceiver to transmit signals to and receive signals from a base station within a dwelling. In some embodiments, the home/away sensor can be housed within a remote device having other functions in addition to home/away sensing, such as emergency call functionality or motion detection among others. In various embodiments, a remote device having home/away functionality can be portable and can, in some embodiments be worn or carried by an individual (e.g. as a pendant, watch, bracelet, pin, necklace, etc.).

In various embodiments, the remote device can be used with a base station component of a monitoring system such as that described in application Ser. No. 11/323,077 as discussed herein. The remote device with home/away functionality can be used to indicate whether the individual is within a certain distance of the base station of the system, for instance, through use of a sensor. In some embodiments, a transceiver, transmitter, and/or a receiver can be used to transmit signals to and/or receive signals from a base station within a dwelling.

In various embodiments, a presence of an indication from a home/away sensor can be taken to mean that the home/away sensor is within range and that the individual possessing the home/away sensor is present in a monitoring area (e.g., in a "home" state). Similarly, in some embodiments, an absence of an indication from a home/away sensor can be taken to mean that the home/away sensor is out of range and that the individual possessing the home/away sensor is not present in a monitoring area (e.g., in an "away" state).

However, if the home/away sensor is not working for some reason (e.g., the individual fell and the home/away sensor broke during the fall), the home/away sensor may indicate that the individual is away from the dwelling even though the individual is still within a predetermined distance to the base station. In such instances, an embodiment can include a logic component of a monitoring system that can use other sensors to cross-check whether the home/away sensor activation is accurate.

For example, one "other" sensor can be an exit door sensor. To verify that the home/away sensor activation is accurate, the exit door sensors of the dwelling can be checked to see if the individual activated them. If one or more of the exit door sensors have been activated, there is a likelihood that the individual did leave the dwelling. On the other hand, if no exit sensors were activated, then there is a likelihood that the individual is still within the dwelling.

In this instance, the logic component can be rules-based, and can initiate a timer which establishes a time period for making the determination. The system can then monitor other sensors (e.g., the exit sensors) within the dwelling to detect any sensor activations and/or review past sensor activations to identify if an exit door sensor was activated within a predetermined time period preceding the activation of the home/away sensor. For such review, the system can include memory to store such information or send the information to a remote server (e.g., at a remote monitoring site), for example.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2.

As will be appreciated, elements shown in the various embodiments herein can be added, exchanged, and/or eliminated so as to provide a number of additional embodiments of value. In addition, discussion of features and/or attributes for an element with respect to one Figure can also apply to the element shown in one or more additional Figures. Also, the figures herein are not necessarily to scale.

FIG. 1 illustrates a monitoring system in which various remote device embodiments can be used. In the illustrated embodiment of FIG. 1, the system utilizes the base station 110 to monitor the activities of a client (e.g., an individual) in and/or around a dwelling through use of a number of sensors 112-1, 112-2, and 112-N.

The base station 110 can also initiate a number of actions based upon a number of rules implemented by the base station 110. These rules use the information obtained from the number of sensors 112-1 through 112-N to determine whether to initiate an action or not.

The base station 110 includes a number of components providing a number of functions, as will be discussed herein. In the embodiment of FIG. 1, the base station 110 is illustrated with respect to its various functionalities. For example, the base station 110 is capable of using rules 116 and/or timers 118 to determine whether to initiate an action 120.

As discussed herein, in some embodiments the base station 110 includes program instructions to receive signals from sensors 112-1 through 112-N that are generated by activation of a sensor 112-1 through 112-N. In some embodiments, signals can be generated in a binary (e.g., on/off) fashion, such that the sensor generates a signal when the object being sensed changes state. For example, with respect to a sensor on a door, one type of sensor that can be provided can operate such that when the door is closed, no signal is generated, but when the door is opened, a signal is generated.

Similarly, when the door is closed again, another signal may be generated. Since the signals can be either on/off, the signals are typically easy to track and the sensors 112-1 through 112-N are inexpensive. However, embodiments of the disclosure are not limited to the use of on/off type sensors and can include various types of sensing devices, including ones whose signal strengths scale to the size of the activation parameter, such as temperature, weight, or touch.

The one or more sensors can be of many different types. For example types of sensors can include, but are not limited to, sensors to indicate the opening and closing of a door and/or drawer; sensors to indicate the movement of objects such as shades and/or blinds; current and/or voltage sensors to monitor appliances, lights, wells, etc.; pressure or fluid flow sensors to indicate the turning on and off of water; temperature sensors to indicate that the furnace is on or off; force sensors such as strain gauge sensors to sense an individual walking over a pad, sitting in a chair, or lying in bed; motion sensors to sense the motion of objects within the dwelling; alert switches/buttons to signal an emergency or client input such as a cancellation request; and sensors to measure the signal strength between multiple sensors.

In some embodiments, the base station 110 can utilize a remote assistance center device (indicated as Remote Access Interface) 114 to inform a third party 122-1 through 122-N that an alert condition exists and that aid may be needed. Aid can be a call to the individual 130, a visit by a third party 122-1 through 122-N to the location of the individual 130, or other such aid. As used herein, "third parties" 122-1 through 122-N can include hospital staff, emergency medical technicians, system technicians, doctors, neighbors, family members, friends of the individual 130, police, fire department, and/or emergency 911 operators.

In the embodiment of FIG. 1, the base station 110 and the remote assistance center device 114 can each be any type of computing device capable of managing the functionality of receiving alert requests and initiating such requests. For example, suitable devices can include personal computers, mainframe computers, system servers, devices having computer components therein, and other such devices.

In some embodiments, the remote assistance center can have a number of operators accessing the remote assistance center device 114 to review and/or respond to alert messages received by the remote assistance center device 114. When a request to initiate an alert is received, the operator monitoring the remote assistance center device 114 can respond, the individual 130 can contact another third party 122-1 through 122-N to respond, and/or the remote assistance center device 114 can contact a third party 122-1 through 122-N to respond, for instance.

In the embodiment where the remote assistance center device 114 can contact a third party 122-1 through 122-N to respond, the remote assistance center device 114 can include a list of third party contacts. These contacts can be compiled from the assistance center and/or from the individual 130, among other sources.

In addition, in some embodiments, the remote assistance center device 114 can use a number of methods to decide which of the other third parties 122-1 through 122-N to contact. For example, the selection of a third party 122-1 through 122-N can be based on the level of severity of the alert or the contacting hierarchy stipulated by the individual 130.

In various embodiments, the third party 122-1 through 122-N receiving the alert can provide a confirmation that the third party is the party intended to receive the alert. This can be a voluntary submission or can be asked for by the remote assistance center device 114.

In various embodiments an alert can be canceled, for example, through use of an alert cancellation sensor activated either by the individual 130 being monitored or by a third party 122-1 through 122-N activating the sensor. The sensor can be one of various sensors within the system.

For instance, the sensor can be a button on the base station 110 and/or portable remote device 126-2 which senses when someone actuates the button. The sensors can be analog and/or digital type sensors and can include logic circuitry and/or executable instructions to transmit logic output to the base station 110.

As illustrated in FIG. 1, the remote assistance center device 114 and a local interface 124 are accessible by a individual 130 (e.g., client). The communication between the devices 110, 112-1 through 112-N, and 124 can be accomplished in various manners.

For example, in the embodiment shown in FIG. 1, the communications can be accomplished by wired (e.g., telephone lines) and/or wireless (e.g., radio interface) communications. Further, in some embodiments, the functionality of these devices can be provided in fewer devices than shown, or in more devices than shown.

In an additional embodiment, system devices 126-1 through 126-N (where "N" represents any number) can also communicate with the base station 110 through the local interface 124. In some embodiments, a system device can be in the form of a key fob 126-1.

The key fob 126-1 can, in some embodiments, provide access to and/or control of at least some of the functions of the base station 110 described herein. In some embodiments, a system device can be in the form of a home/away sensor 112-5. Embodiments of the home/away sensor 112-5 are discussed in greater detail herein.

In some embodiments, a logic component can be used to control the functions of the base station 110. For example, the logic component can include executable instructions for providing such functions as handling received information from the sensors in the system, time-stamping received information such as sensor activation and/or system health functionality, among others. In some embodiments, the logic component can include RAM and/or ROM, a clock, an input/output, and a processor, among other things.

In some embodiments, the logic component can be designed such that a first condition is to be met before beginning to monitor a second condition. For example, a first sensor activation can be detected and then a timer can be started to monitor the time elapsed until another sensor activation from the same sensor and/or from a different sensor. In some embodiments, the first condition can be represented by receiving a first signal from a first sensor and the second condition can be represented by waiting for a second signal from at least one of the number of sensors of the system.

In some embodiments, a remote device can be used with the base station 110. The remote device can be portable and be carried or worn by the individual 130, as discussed herein. Portable remote devices 126-2 can be any type of device that is portable and that can provide the described functionalities.

Examples can include basic devices that have a sensor and the capability to provide power to the sensor, up to complex devices, having multiple functions. Examples of complex portable remote devices 126-2 can include mobile telephones and portable computing devices, such as personal digital assistants (PDAs) and the like.

In some embodiments, the portable remote device can have home/away functionality to indicate whether the individual 130 is within a certain distance of the base station 110 of the system, for instance, through use of a sensor (e.g., sensor 112-5). In some embodiments, a transceiver, transmitter, and/or receiver can be used to transmit signals to and/or receive signals from the base station 110 within the dwelling.

As used herein, a transmitter and a transceiver can be used interchangeably if a transmission functionality is desired. Additionally, a receiver and a transceiver can be used interchangeably if a reception functionality is desired.

In some embodiments, the home/away functionality can be accomplished using a home/away sensor 112-5 included in the portable remote device 126-2. The home/away sensor 112-5 can be used to indicate that an individual 130 is present or not within a monitored area based upon the home/away sensor's 112-5 distance from the base station 110.

For example, if a short range communication type of sensor is used, when the home/away sensor 112-5 is out of range of the base station 110, the system can determine that the client is away. The range of use for the portable remote device 126-2 can be designed to be between one hundred and two hundred feet from the base station 110. Short range communication types of sensors can include IEEE 802.15.4 and/or IEEE 802.11 protocols, among others.

In some embodiments, the home/away sensor 112-5 can be an inexpensive binary sensor, as discussed herein. For example, the home/away sensor 112-5 can be designed to generate a signal "on" when the individual 130 is within the monitoring area (e.g., "home"), and "off" when the individual 130 is outside of the monitoring area (e.g., "away").

Locating and/or confirming the presence of a portable remote device 126-2 with a home/away sensor 112-5 within a monitored area can be accomplished in various manners, such as by initiating a ping signal from the transceiver to the portable remote device 126-2. In such a case, the portable remote device 126-2 can also include a transceiver and can receive the ping signal and can respond.

The transmission of the ping signal can be by any means, such as via a radio frequency, and the like. In some embodiments, a transmitter and/or a receiver can receive the ping signal and can respond. If a response to the ping signal is received by the base station 110, then the executable instructions can interpret that to mean that the individual 130 is within the signal range of the base station 110. If other sensors have not been activated within a predetermined amount of time and a ping response is received, executable instructions can initiate an alert to the individual 130, as discussed herein.

In some embodiments, the logic component can include a set of rules for determining with more certainty whether the individual 130 is really home or away. For example, if the home/away sensor 112-5 is not present, in some embodiments, after a number of cycles and/or rechecks, the logic component can check a number of sensors 112-1 through 112-N of the system to identify whether any sensor, a certain sensor, or certain sensors have been activated during a particular time.

For example, in some embodiments, the system checks an exit sensor to identify whether the exit sensor was activated within a particular period of time before the home/away sensor 112-5 is indicated as being "away." Examples of other sensors include motion sensors, sensors on the interior/exterior/garage doors, sensors on the individual's 130 automobile, and the like.

In some embodiments, if the home/away sensor 112-5 is indicated as being "away," but the logic component determines that a number of other sensors 112-1 through 112-N have not been activated, the remote assistance center device 114 can send an emergency alert. Similarly, in some embodiments, if the home/away sensor 112-5 is indicated as being "home," but the logic component determines that a number of other sensors have not been activated, the remote assistance center 114 can send an emergency alert. The logic component can include rules based software, firmware, and/or hardware to make this determination.

Such embodiments enable the system to avoid a false alert initiation based upon the absence of sensor activations during a prolonged period. Such embodiments also enable the system to determine if the individual 130 is still inside the dwelling even though the system indicates the home/away sensor 112-5 is not present. This is beneficial in the situation where the individual 130 has fallen and broken the home/away sensor 112-5, but remains in the dwelling, but may be unable to reach an emergency sensor, for example.

As discussed herein, the portable remote device 126-2 can communicate with the base station 110 using short range communication signals. In these embodiments, the portable remote device 126-2 can use a short range communication signal and the local interface 124 can be incorporated into the base station 110.

Additionally, in some embodiments, the portable remote device 126-2 can utilize a long range communication signal to communicate to the base station 110 114. In these embodiments, the local interface 124 can be a mobile device such as a mobile telephone that can send the instructions from the portable remote device 126-2 to the base station 110 114. In such embodiments, the portable remote device 126-2 can be separate from, associated with, or included in the mobile device.

Additionally, the portable device can include executable instructions to enable the portable remote device 126-2 to communicate with the mobile device in order to instruct the mobile device how to forward its base station message to the base station 110. In some embodiments, the base station 110 can include executable instructions to enable a short range communication signal to be translated into a long range wireless signal when the distance between the portable remote device 126-2 and the base station 110 is greater than the distance between the portable remote device 126-2 and the mobile telephone.

In addition to an on/off sensor, in some embodiments the portable remote device 126-2 can also include a motion sensor to sense motion of the individual 130. By incorporating a motion sensor into the portable remote device 126-2, the monitoring system is less likely to sense periods of inactivity.

For example, although an individual 130 may be sitting on a chair for a prolonged amount of time, the individual 130 may move the portion of the body is wearing the portable remote device 126-2 while sitting, which would signal activity to the monitoring system despite the relative inactivity of the individual 130. In addition, in some embodiments, the remote assistance center device 114 can be configured to issue an alert after a predetermined amount of time if the motion sensor has not been activated within that predetermined amount of time.

The time periods used by the system to determine whether to initiate an alert can be predetermined by the manufacturer of the system, the installer, and/or the client, in various embodiments. Additionally, the periods can be designed to be updated during the lifetime of the device.

The portable remote device 126-2 can be equipped with several different features and functionalities. In some embodiments, for example, the determination of whether the individual 130 is home or away can be accomplished by identifying the location of the home/away sensor 112-5. In such embodiments, the home/away sensor 112-5 can be communicating via a long range communication type with the base station 110 and the home/away sensor 112-5 can be located in various manners including via tracking of the communication signal, such as cellular triangulation, or other such mechanisms.

In an additional embodiment, the portable remote device 126-2 can also be used for identification purposes with the base station 110. For example, the portable remote device 126-2 can include a magnet and/or reed switch to unlock a door and/or activate a light when the individual 130 approaches the door and the base station 110 receives a signal from the portable remote device 126-2 of the individual 130.

As discussed herein, the logic component of the base station 110 is designed as a rules based device. In some embodiments, the logic component can be designed such that the first sensor is the home/away sensor 112-5 and the first rule states that if the home/away sensor 112-5 is absent, then the logic component can initiate a first action, for example, locking a door.

In another embodiment, the logic component can be designed such that the first sensor is the home/away sensor 112-5 and the first rule states that if the home/away sensor 112-5 is present, then the logic component can initiate a first action, for example unlocking a door. In addition, in various embodiments the logic component can be designed such that the first sensor and the second sensor are the home/away sensor 112-5 and the first rule states that if the home/away sensor 112-5 is present, then the first action is to unlock the door, and the second rule states that if the home/away sensor 112-5 is absent, then the second action is to lock the door.

As discussed herein, in some embodiments the portable remote device 126-2 can include a button or switch, for example, that can be used to signal an alert. The portable remote device 126-2 can also include an activation mechanism that can be used to cancel an alert initiated by the portable remote device 126-2 and/or by the base station 110. In some embodiments, the individual 130 or a third party 122-1 through 122-N can confirm that an alert has been received from the base station 110 through use of an activation mechanism, such as a button or switch.

In some embodiments, the number of sensors 112-1 through 112-N inside or outside the dwelling can be designed to measure the signal strength between the number of sensors 112-1 through 112-N and the home/away sensor 112-5 included with the portable remote device 126-2. In addition, the logic component can include executable instructions to locate the home/away sensor 112-5 based on the largest signal strength between the number of sensors 112-1 through 112-N and the home/away sensor 112-5.

In an additional embodiment, the number of sensors 112-1 through 112-N can include a task sensor, where the task sensor is associated with a task assigned to the individual 130. For example, in some embodiments the individual 130 is assigned the task of retrieving a beverage.

In such embodiments, the task sensor would be the sensor that is activated when the refrigerator door is opened. The logic component can thus be designed to couple the task to the task sensor and to initiate a task-complete action when the task sensor is activated. In some embodiments, the task-complete action can be to send a signal to the remote assistance center device that the task was completed successfully. Other task-complete actions may also be taken. In some embodiments, one or more sensors can be used to identify when a task is compete and/or in progress. Such embodiments can accomplish these tasks, for example, by monitoring the actuation of one or more sensors, the time between sensor activations, and other such suitable manners.

In some situations, more than one individual 130 being monitored lives inside a single dwelling. In this situation, the home/away sensor 112-5 and/or portable remote device 126-2 can be equipped with an identification tag. In some embodiments, the logic component can be designed to initiate a task-complete action when the task sensor is activated and when the signal strength between the home/away sensor 112-5 with the correct identification tag is larger than the signal strength between the home/away sensor 112-5 with a different identification tag and the task sensor.

Figure 2:
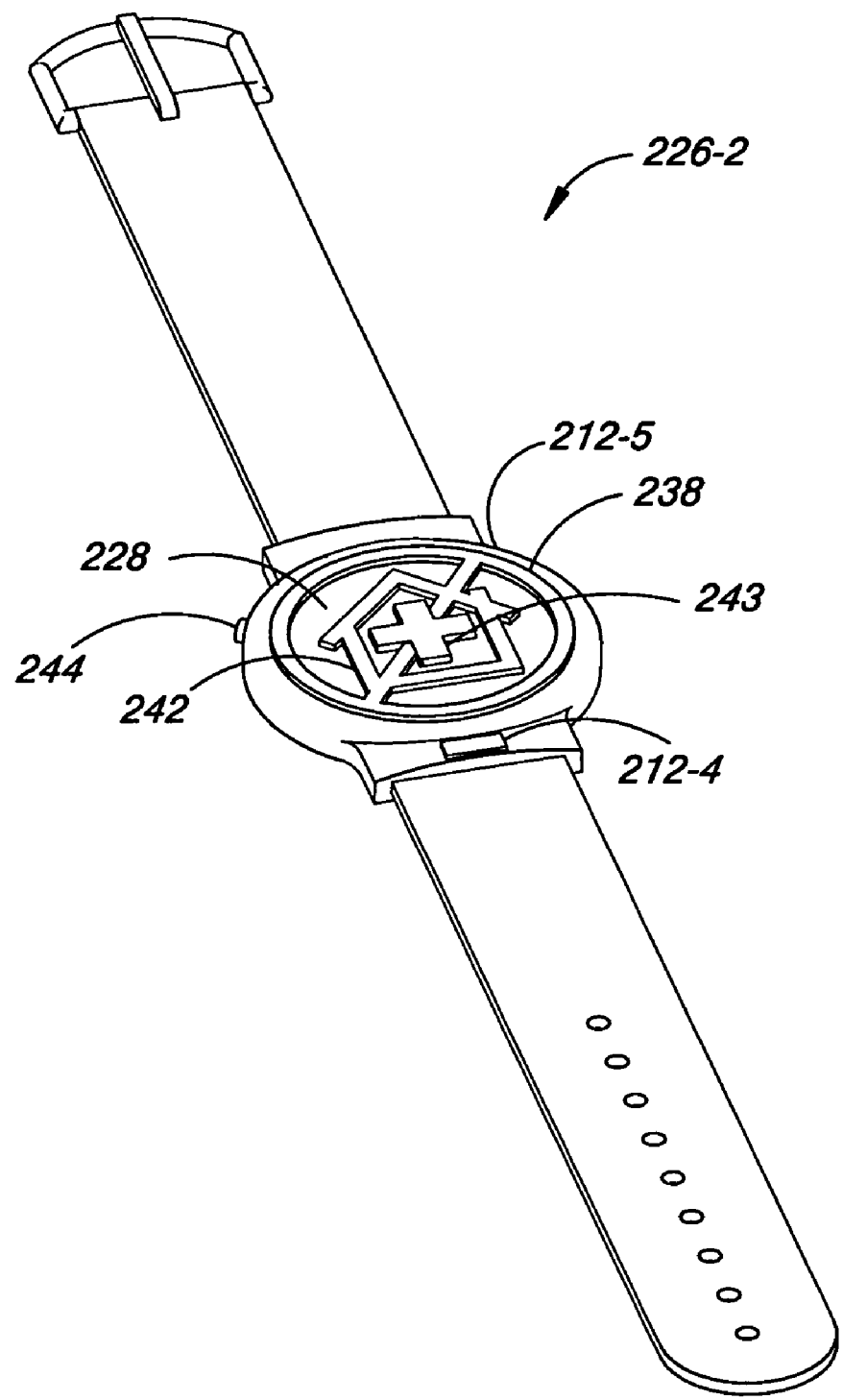
FIG. 2 illustrates an embodiment of a remote device.

FIG. 2 is an illustration of an embodiment of the portable remote device 226-2. In this embodiment, the portable remote device 226-2 is in the form of a wrist band similar to a watch. Other forms of the portable remote device 226-2 are also possible, including a pendant or pocket clip.

Also, in some embodiments, the portable remote device 226-2 can be a card that is incorporated into a mobile telephone or other device. In some embodiments, the portable remote device 226-2 can be convertible from a watch to a pendant and/or pocket clip. In these embodiments, the r portable remote device 226-2 can be equipped with additional attachments such as a clip to hook onto a belt loop and/or a chain so that the remote device 226-2 can be worn around the neck of an individual.

As discussed herein, the portable remote device 226-2 can be equipped with components including, but not limited to, a transceiver, a transmitter and/or a receiver, an antenna, a power source, a microprocessor, memory, input devices, and/or output devices such as lights, speakers, and/or buzzers.

The portable remote device 226-2 is typically compact in size to enable the client to wear it on his or her body without being encumbered. For example, in some embodiments the portable remote device 226-2 can be less than two (2) inches long, less than one and three quarter (1.75) inches wide, and less than seven-tenths (0.7) inches tall.

In addition, the portable remote device 226-2 can be water resistant to three (3) meters, so that the client can wear it while bathing or doing household chores, such as washing dishes or cleaning. The portable remote device can also be tolerant to sweat and common household chemicals that are appropriate for skin contact. In some embodiments, portions of the remote device 226-2 can be made of a rigid polymer, while other portions of the remote device 226-2 can be made of a flexible polymer.

For example, the base plate, battery cover, and/or pendant clip can be made of a rigid polymer, such as high density polyethylene (HDPE). In addition, the top of the portable remote device 226-2 can be made of a flexible polymer, as discussed herein.

In some embodiments, the output device on the portable remote device 226-2 is a display. The display can include a screen with refreshing content, such as a computer screen, or can be a number of symbols that are emphasized at different times to indicate different states of the device, conditions of the system, and/or different messages about the health of the individual and/or system.

In some embodiments, the display can be made of a flexible polymer to allow for the individual to be able to push a button in the center of the display. In addition, the display can be translucent to act as a light pipe to bring light from different light emitting diodes (LEDs).

In various embodiments, the display can be configured using a liquid crystal display (LCD) where messages can be sent and shown on the display. Also, in some embodiments, the symbol of message on the display can be accompanied by an alarm and/or buzzer. In an additional embodiment, the portable remote device can communicate messages to the individual via a sound or physical alarm without a visual message.

FIG. 2 illustrates some embodiments of a display on the remote portable device 226-2. As illustrated, the display includes a house symbol 242, a plus-sign symbol 243, and a circle with a line through the house 238. In this embodiment, the symbols can light up separately and/or simultaneously to indicate different messages from the base station.

For example, the portable remote device 226-2 can display an out of range message by lighting the circle with a line through the house symbol 238 in red when system sensors have not monitored movement for a predetermined amount of time. In addition, in other embodiments, the remote portable device 226-2 can be configured to alert the client to situations that require attention, such as in-home alerts, low battery, and/or stages of emergency help, as discussed herein.

In some embodiments, the portable remote device 226-2 can include an emergency call mechanism in the form of a button or switch. When the button is actuated (i.e. "pressed"), the portable remote device can transmit a wireless signal indicative of an emergency to the base station. The base station can then signal the remote assistance center device, which can issue an emergency alert, as discussed herein.

In addition, the portable remote device 226-2 can display an acknowledgement message once an action to initiate contact to the remote assistance center device has been undertaken. For example, once the emergency mechanism, or sensor, 212-4 is activated, the background 228 of the portable remote device 226-2 can flash yellow to signify that the button 212-4 has been pressed and that the portable remote device 226-2 was able to communicate with the base station. In some embodiments, the background 228 can flash yellow using a yellow LED.

In some embodiments, the logic component can include executable instructions to allow for a cancellation period where the individual being monitored can cancel the emergency call and subsequently the flashing yellow in the background 228 can stop. The cancellation period can last for a predetermined amount of time, for as long as it takes the remote assistance center device to contact a third party, as discussed herein, or the individual can cancel the emergency call at any time after the emergency call mechanism has been activated.

In addition, as illustrated in FIG. 2, the portable remote device 226-2 can display an acknowledgement or message-relayed message by lighting the plus-sign symbol 243 in red. In such embodiments, the plus-sign symbol 243 flashes red when the base station makes the actual call to a third party to summon aid. In this embodiment, the plus-sign symbol 243 will continue to flash until the call is either cancelled by the individual or when help arrives. In some embodiments, the plus-sign symbol 243 can flash red using a red LED.

Some embodiments can use the short-range communication type for the emergency call functionality. Such embodiments can include a portable device 226-2 having an emergency call sensor (e.g., button) 212-4 and/or a home/away sensor 212-5. In various embodiments, if the system determines that the individual is "away," then the system can transmit an out-of-range message to the portable remote device 226-2 having an emergency call functionality. This out-of-range message can indicate to the individual that the emergency call functionality is not likely to work, since it is out-of-range.

Additionally, in various embodiments the device can use a long range communication type for the emergency call functionality. In this way, the emergency call function could be used while the individual is at the store or down the street from their dwelling and, if used with a system having a short range home/away sensor 212-5, the system could also be indicating that the client is away. Further, through use of a longer range communication type, it may also be possible to locate the client based upon the communication signal as described herein.

In various embodiments the logic component can be designed to initiate a check-in rule based functionality using the portable remote device 226-2. Such embodiments can include an action in the form of a warning message displayed on the portable remote device 226-2 being initiated at a predetermined time interval.

For example, the portable remote device 226-2 can display a warning message by lighting the house symbol 242 in yellow. The warning message as used herein is used to check-in with the client when the client desires this functionality. In some embodiments, the client can personalize the logic component to initiate a check-in rule based functionality based on the client's needs. For example, the check-in rule based functionality can remind the client to take medication, to go to an appointment, and/or to watch a favorite television program.

In such embodiments, the client can, for example, set a predetermined time and/or time interval for the check-in rule based functionality. (e.g., the client could choose for the check-in to occur at 8:00 am daily). In such an example, at 8:00 am every day, the portable remote device 226-2 would display the warning message by lighting the house symbol 243 in yellow, for example.

The client would then have a predetermined time range to initiate an action to acknowledge the warning and the check-in rule based functionality would reset to check-in at the next predetermined time. If the client did not initiate an action to acknowledge the warning within the predetermined time range the check-in rule based functionality would initiate further warnings, as discussed in more detail herein.

In some embodiments, the system could initiate a warning to the client using the portable remote device 226-2. For example, the portable remote device 226-2 can display a warning message by lighting the house symbol 242 in yellow during periods of inactivity. The client then has a predetermined time period, such as ten minutes, to activate the acknowledgement sensor 244 before the system contacts a remote third party. The logic component designed to initiate a warning to the client during periods of activity can be used in conjunction with and/or separate from the check-in rule based functionality.

The embodiments of the portable remote device 226-2 discussed herein can incorporate many features such as the signal strength measurements, identification tag memory, emergency call functionality, the check-in rule functionality, and/or the out-of-range message display. Consequently, as the number of features increases, the demand on the power source will increase. Therefore, in various embodiments, the portable remote device is designed to have power saving functions, as discussed herein.

In some embodiments, the home/away sensor 212-5 is activated when the individual moves in and out of the base range, as such, the system can be configured to stand down until the home/away sensor 212-5 is once again in range.

In some embodiments, the portable remote device 226-2 can be designed with an adjustable update rate. An adjustable update rate refers to the amount of times the home/away sensor 212-5 signals to the base station and/or the length of the signal sent by the home/away sensor 212-5. By decreasing the amount of signals sent to the base station and/or decreasing the length of time the signal is sent, the power source (i.e. battery) lifetime is increased.

In some embodiments, the portable remote device 226-2 can include an automatic home/away sensor 212-5 update rate adjustment. In this embodiment, when the home/away sensor 212-5 is out of range with the base station, after a prescribed number of missed communications with the base station, the home/away sensor 212-5 adjusts the update rate to decrease the number of attempted signal communications sent by the home/away sensor. Additionally, the home/away sensor 212-5 can be configured to return to the normal update rate when the home/away sensor 212-5 receives an acknowledgement from the base station.

In some embodiments, the portable remote device 226-2 can include an automatic home/away sensor update rate adjustment where the length of the signal sent by the home/away sensor 212-5 is adjusted. For example, when the home/away sensor 212-5 is out of range with the base station, after a prescribed number of missed communications with the base station, the home/away sensor 212-5 adjusts the update rate to decrease the length of time the signal is sent.

In some embodiments, the home/away sensor 212-5 sends a signal to the base station for a first predetermined time of five (5) seconds at a first predefined time interval of thirty (30) seconds. When the number of missed communications attempted by the home/away sensor 212-5 reaches five (5), the home/away sensor 212-5 sends a signal to the base station for a second predetermined time of two hundred (200) milliseconds at a second predefined time interval of five (5) minutes.

In addition, in some embodiments, the remote device can include an "awaken" mechanism, where activating the awaken mechanism transmits a wireless signal indicative of a return of the portable remote device 226-2 to within the base range of the base station. When the awaken mechanism is activated, the home/away sensor 212-5 can begin to send signals to the base station at the first predetermined amount of time if five (5) seconds at the first predefined time interval of thirty (30) seconds. Other first and second predetermined times of signal length and first and second predefined time intervals are also possible.

In some embodiments, the home/away sensor 212-5 can be constructed to periodically check-in with the base station device, such as by sending a ping signal to the base station device via radio frequency or other such manner. In such embodiments, the home/away sensor 212-5 can be provided with energy saving executable instructions that allow the home/away sensor 212-5 to be in "sleep mode," where power usage is reduced, and then to "awaken" periodically to send a ping signal to the base station device. Once the signal is sent, the sensor 212-5 can then return to "sleep mode." When in "sleep mode" the client can awaken the sensor 212-5 manually, for instance, by pushing an emergency button 212-4.

In an additional embodiment, a buck boost circuit can be added to the portable remote device 226-2. A buck boost circuit can minimize the amount of voltage needed to operate the remote device 226-2. By minimizing the voltage, the remote device 226-2 is able to use more of the battery reserve, and consequently have a longer battery life.

In some embodiments, the portable remote device 226-2 can be designed to have a client-replaceable battery that can be replaced by the client without the need for special tools. An exemplary battery for use in this embodiment can be a standard CR2430 2V lithium battery. In this embodiment, the power source can last on low power for approximately three months.

In yet another embodiment, the portable remote device 226-2 can display a low battery warning. For example, when the battery is low, the background 228 can flash orange to signify that the battery is low. In addition, when the battery is too low to support functionality, the background 228 can be lit in orange until the battery is completely drained. In some embodiments, the background 228 can be lit in orange using orange LEDs.

Figure 3:
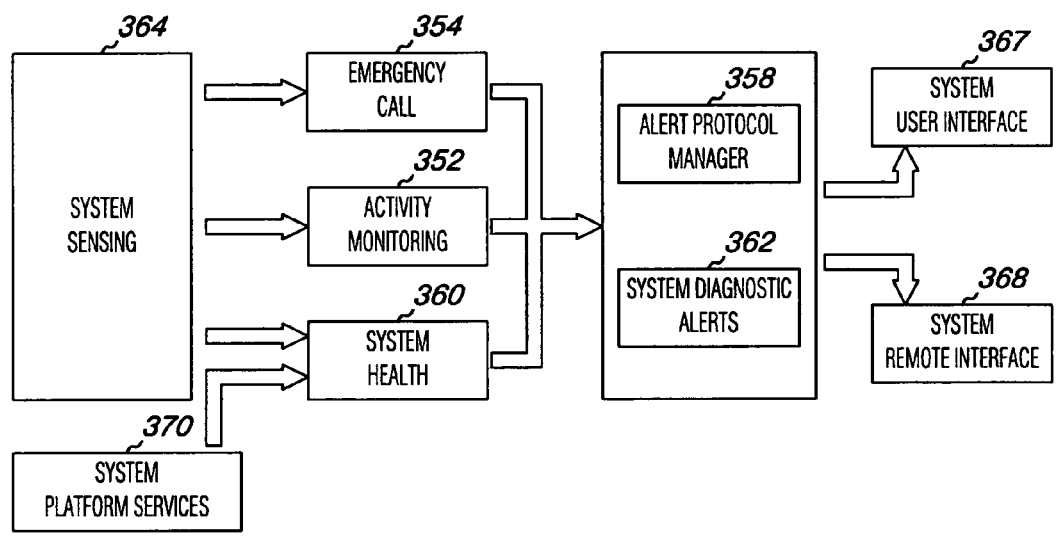
FIG. 3 illustrates an embodiment of base station data flow.

FIG. 3 illustrates an embodiment of base station data flow. This diagram illustrates the flow of information from various parts of the system. In the embodiment shown in FIG. 3, the system sensing information 364 can be used in a variety of functions provided by the system.

For example, system sensing information can be used to support emergency call functions 354, activity monitoring functions 352, and system health functions 360, among others. Each of these functions (i.e., 352, 354, and 360) utilizes information about either a sensor or an activity of an individual that activates a sensor.

The blocks 352, 354, and/or 360 can process and interpret information from system sensing block 364 in order to provide information to the alert protocol manager functionality 358, and a system diagnostic alert protocol functionality 362. These functionalities can be provided at the base station and/or at a remote location, for example. Individually, blocks 352, 354, or 360 can pass system information directly to the alert protocol manager 358, or can process the information itself to determine the need to initiate an alert request or other action request to the alert protocol manager 358.

The alert protocol manager 358 can initiate an alert upon a request from 352, 354, or 360, or can further process the information received from 352, 354, or 360 to determine whether to initiate an alert or other action.

In the embodiment illustrated in FIG. 3, the initiation of an alert by the alert protocol manager 358 can be implemented through use of functions within the system client interface 367 and/or the system remote interface 368. In various embodiments, the system remote interface 368 can be a call center computer, such as a computer at an emergency call center. For example, an alert process can include a notification of the client that an alert will be or has been initiated. This can be brought to the client's attention to allow the client to cancel the alert if the need for an intervention does not exist or has passed. In such cases, the system client interface can be used to indicate the impending or existing alert condition and/or can be used by the client to confirm and/or cancel the alert.

The system remote interface can be used to contact a third party, such as a remote assistance center device to inform the third party that an alert condition exists and that aid may be needed. Aid can be a call to the client of the system, a visit by a third party (e.g., doctor, emergency medical personal, system technician, etc.) to the location of the client, or other such aid, as discussed herein.

Similarly, system information can be provided from the system platform services block 370 to the system health block 360. This information can be used to determine whether to issue an alert for a fault in the system, for a software/firmware update, or the like. The system diagnostic alert block 362 can be used to issue such an alert. This alert can then be effectuated through the system client interface 367 and/or the system remote interface 368.

For example, if a sensor has to have a battery changed, the alert can be sent to both the individual and a third party (e.g., via blocks 367 and 368). If the client changes the battery, the alert can be canceled and notification of the cancellation can be provided to the third party.

Figure 4:
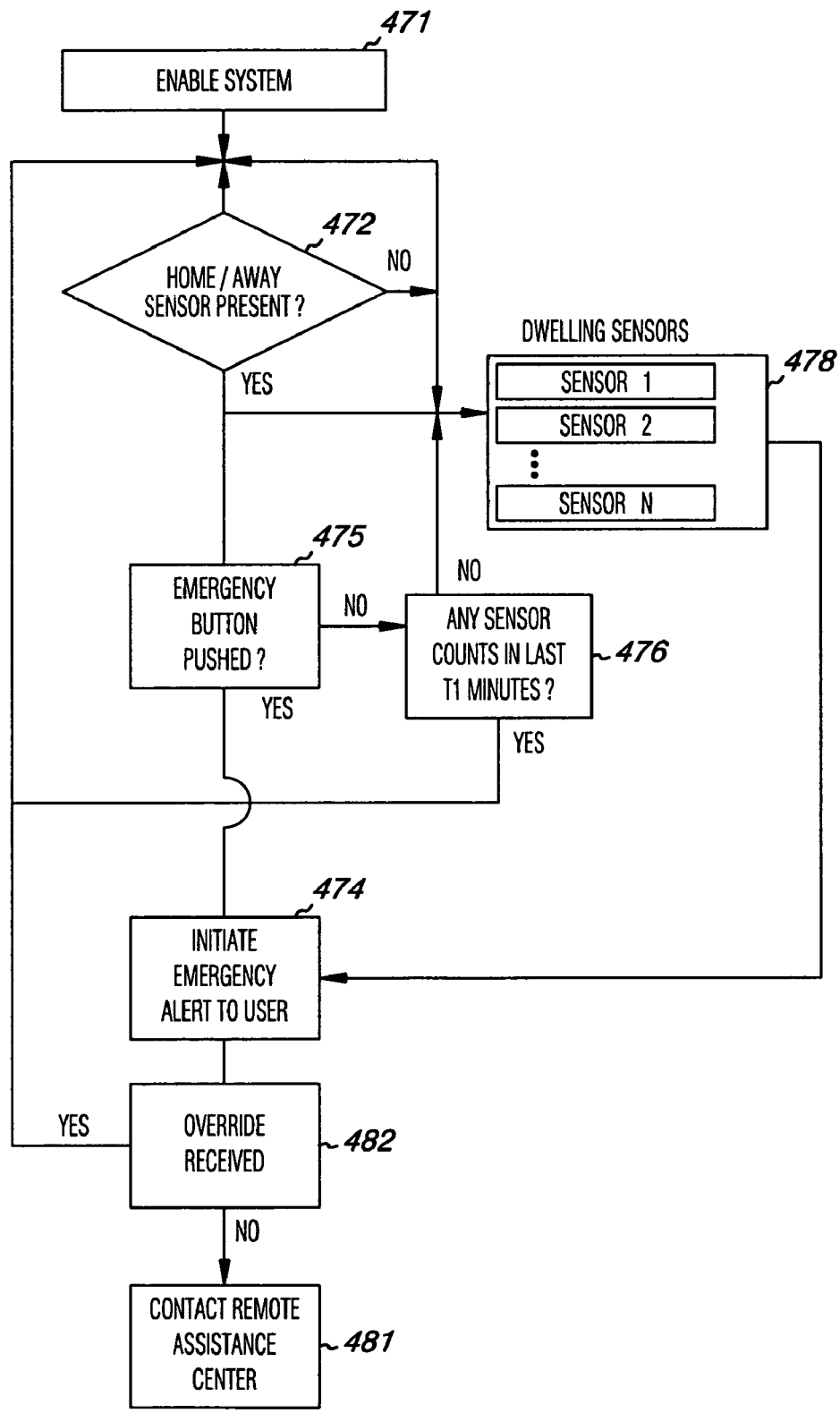
FIG. 4 illustrates an embodiment of activity monitoring alert protocol management.

FIG. 4 illustrates one embodiment for monitoring activity. Although the embodiment illustrated in FIG. 4 has arrows indicating a flow path, this is meant to be an example of flow and should not be viewed as limiting. Unless explicitly stated, the embodiments described herein are not constrained to a particular order or sequence. Additionally, some of the described embodiments and elements thereof can occur or be performed at the same point in time. Embodiments can be performed by executable instructions such as software and/or firmware.

FIG. 4 illustrates an embodiment of activity monitoring alert protocol management. The system can include other rule based protocol management operations than the one provided herein as an example of such rule based protocols. Further, the multiple sensors inside the dwelling are identified generally; a more detailed description of the sensor protocol management is further described in U.S. application Ser. No. 11/323,077 entitled "Monitoring Activity of an Individual", of which this disclosure is a continuation-in-part.

The embodiment of FIG. 4 can be accomplished by a number of executable instructions and/or through use of logic circuitry. In the embodiment illustrated in FIG. 4, the system is enabled at block 471. In such rule based systems, each possible result includes an action, such as to wait for another condition to be met or to perform an action, etc.

The home/away sensor can be used to indicate that an individual to be monitored is present or not within the monitoring area. In this way, if the individual is not present then false alert initiation based upon the absence of sensor activations during a prolonged period can be suppressed, among other benefits, as discussed herein.

In the embodiment illustrated in FIG. 4, the home/away sensor is checked to identify if it is present at block 472. If it is not, then the system can cycle and recheck to see if the sensor is present at that later time.

In some embodiments, the system can report an error after the system has accomplished a number of such cycles and rechecks. Additional system checks, including sensor checks can be accomplished at this point in the process as well as at other points in the process.

As discussed herein, if the home/away sensor is not present, in some embodiments, after a number of cycles and/or rechecks, the system can check a number of sensors of the system to identify whether any sensor, a certain sensor, or certain sensors have been activated during a particular period of time. For example, in some embodiments, the system checks an exit sensor to identify whether the exit sensor was activated within a particular period of time before the home/away sensor is indicated as being "away".

In the embodiment illustrated in FIG. 4, if the home/away sensor is indicated as present, the system can begin checking a number of sensors within the system. In such embodiments, the system checks to see if an emergency call button has been pressed at block 475. If it has been pressed, an alert announcement can be initiated to the individual being monitored, at block 474. The announcement can be audio, visual, and/or physical in nature.

In some embodiments, the system can provide the individual with an opportunity to override the emergency alert, at block 482. If the override is received, the system returns to its normal monitoring cycle. If not, the remote assistance center can be contacted, at block 481. The attempts to contact can be continued indefinitely, or for a period of time, until the alert has been acknowledged.

If the emergency sensor has not been activated at block 475, the system can check a number of other sensors of the system to identify whether any sensor, a certain sensor, or certain sensors have been activated during a particular period of time (e.g., parameterized as Ti minutes in this embodiment), at block 476. If no sensors have been activated during that period, then the system checks the dwelling sensors 478, for example a chair or bed sensor, to see if the individual on a chair or in a bed based upon chair and/or bed sensor activation information.

If no sensors 478 have been activated, the system announces the initiation of an alert to the individual at block 474. If an override is not received at block 482, the remote assistance center is contacted at block 481. With regard to the embodiment of FIG. 4, the various sensors of the system can be checked at various times during the monitoring of the system. For example, one or more of the sensors 478 can be periodically checked after the system checks whether the home/away sensor is present.

Further, in some system embodiments, if a sensor is malfunctioning or has become inoperable, a combination of sensors can be used to identify whether or not an alert should be initiated. For example, if the home/away sensor is not present, the system can check on or more other sensors to see if the other sensors confirm that the client is away from the base station, as discussed herein.

As another example, an activation of a first sensor can be associated with a simultaneous activation of a second sensor. For instance, a sensor indicating the opening of a kitchen cupboard can be associated with a motion sensor in the kitchen.

In this instance, the system looks for the activation of the kitchen cupboard sensor and the kitchen motion sensor during a defined time period (e.g., nearly simultaneous, within a few seconds, etc.). If these sensors do not activate within the time period, then the system can identify the sensor that did not activate as possibly malfunctioning.

The time periods used by the system to determine whether to initiate an alert can be predetermined by the manufacturer of the system, the installer, and/or the client, in various embodiments, as discussed herein. Additionally, the periods can be designed to be updated during the lifetime of the device.

This updating can be accomplished through use of a number of different mechanisms. For example, logic circuitry can be used to change (e.g., increment, decrement, or substitute) a timer value in order to keep the value within an acceptable range. The system can also be updated to change a rule. For example, a rule can be changed in order to change how the system checks system health, determines whether an action should be taken, or determines whether to reset a timer. Such time value and rule changes can be accomplished by hardware and/or executable instructions.

Further, in various embodiments, the executable instructions and/or, in some embodiments, the logic of the portable device can be updated. For example, this can be accomplished wirelessly via communication with the base station, among other updating methods.

As discussed herein, locating and/or confirming the presence of a portable remote sensor such as a wearable sensor within the monitored area can be accomplished in various manners, such as by initiating a ping signal from the transceiver to the portable remote sensor. In such a case, the portable remote sensor can also include a transceiver and can receive the ping signal and can respond. The transmission of the ping signal can be by any means, such as via a radio frequency, and the like. In some embodiments, a transmitter and/or a receiver can receive the ping signal and can respond.

If a response to the ping signal is received by the base station device, then the executable instructions can interpret that to mean that the individual is within the signal range of the base station device. If a deviation in a behavior routine has been identified and a ping response has been received, executable instructions can initiate an alert to the individual as has been discussed herein.

As discussed herein, if no response is obtained from the individual, then the executable instructions can determine which third party to contact. Other sensors can be used in combination with, or instead of, a sensor worn by the individual to determine whether the individual is within the dwelling. Examples of other sensors include, motion sensors, sensors on the interior/exterior/garage doors, sensors on the individual's automobile, and the like.

Although specific embodiments have been illustrated and described herein, those of ordinary skill in the art will appreciate that an arrangement calculated to achieve the same techniques can be substituted for the specific embodiments shown. As one of ordinary skill in the art will appreciate upon reading this disclosure, various embodiments of the invention can be performed in one or more devices, device types, and system environments including networked environments.

Combination of the above embodiments, and other embodiments not specifically described herein will be apparent to those of skill in the art upon reviewing the above description. The scope of the various embodiments of the disclosure includes other applications in which the above structures and methods can be used. Therefore, the scope of various embodiments of the disclosure should be determined with reference to the appended claims, along with the full range of equivalents to which such claims are entitled.

In the foregoing Detailed Description, various features may have been grouped together in a single embodiment for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A system for monitoring activity, comprising:
 a remote device comprising:
  a home/away sensor to be activated by an individual, wherein the individual is considered present when the base station receives signals from the home/away sensor and another sensor indicates the presence of the individual in a dwelling and the individual is considered absent when the base station does not receive signals from the home/away sensor and another sensor indicates an exit of the individual from the dwelling; and
  a transmitter actuated by the home/away sensor for transmitting a wireless signal indicative of an activation of the home/away sensor;
 a local interface, where the local interface receives the wireless signal from the transmitter associated with the remote device; and
 a base station operably coupled to the local interface, comprising:
  a receiver for receiving signals from a number of sensors to be activated by an individual; and
  a logic component to:
   institute multiple rules for determining whether to initiate an alert based upon one or more activations of the home/away sensor.

2. The system of claim 1, wherein the logic component is designed to:
- initiate a first rule based upon an identification of a first sensor activation;
- initiate a first timer for monitoring a sensor activation according to the first rule;
- initiate a second timer for monitoring the time between a first sensor activation and at least one second sensor activation according to the first rule; and
- determine whether an action should be initiated based upon the analysis of whether the first rule has been met.

3. The system of claim 2, wherein the logic component is designed to initiate the first rule based upon the identification of the first sensor activation wherein the first rule states that if the first sensor activation is detected, wait a predetermined time for a second sensor activation.

4. The system of claim 3, wherein the first rule further states, if the second sensor activation is not received then initiate an action in the form of a warning message displayed on the remote device.

5. The system of claim 2, wherein the first sensor is the home/away sensor and wherein the logic component is designed to initiate the first rule based upon the identification of absence of the home/away sensor.

6. The system of claim 5, wherein the first rule states that if the home/away sensor is absent, then initiate a first action.

7. The system of claim 6, wherein the first action is locking a door.

8. The system of claim 2, wherein the first sensor is the home/away sensor and wherein the logic component is designed to initiate the first rule based upon the identification of presence of the home/away sensor.

9. The system of claim 8, wherein the first rule states that if the home/away sensor is present, then initiate a first action.

10. The system of claim 9, wherein the first action is unlocking a door.

11. The system of claim 2, wherein the number of sensors can measure a signal strength between the number of sensors and the home/away sensor.

12. The system of claim 11, wherein the logic component is designed to locate the individual based on the largest signal strength between the number of sensors and the home/away sensor.

13. The system of claim 11, wherein the individual is assigned a task and the number of sensors includes a task sensor, wherein the logic component is designed to couple the task to the task sensor and initiate a task-complete action when the task sensor is activated.

14. The system of claim 13, wherein the home/away sensor includes a first identification tag, where the logic component is designed to initiate the task-complete action when the task sensor is activated and the signal strength between the home/away sensor with the first identification tag and the task sensor is larger than the signal strength between the home/away sensor with a second identification tag and the task sensor.

15. The system of claim 2, wherein the logic component is designed to initiate a check-in rule, where a first action is initiated at a predetermined time interval.

16. The system of claim 15, wherein the first action is a warning message displayed on the remote device, and the remote device further comprises an acknowledgement mechanism that when activated transmits an acknowledgement to the base station.

17. The system of claim 16, wherein the check-in rule further states:
- if no acknowledgement is received, then wait a first predetermined time period before initiating the first action again;
- if no acknowledgement is received after initiating a first predefined number of actions, then wait a second predetermined time period before initiating the first action again;
- if no acknowledgement is received after initiating a second predefined number of actions, then a second action is initiated, where the second action is to initiate contact to a remote site.

18. A portable remote device, comprising:
- a home/away sensor to be activated by an individual;
- a transmitter actuated when the home/away sensor is activated for transmitting a wireless signal indicative of an activation of the home/away sensor to a base station, where the transmitter transmits signals from the home/away sensor for a defined duration during a time period and transmits signals for a shorted defined duration during an extended time period when the base station has not received the previous three signal transmissions;
- a receiver for receiving a wireless signal from the base station; and
- a display, where the display communicates messages indicative of the wireless signal received from the base station and the portable remote device is worn on a body of the individual.

19. The portable remote device of claim 18, wherein the portable remote device further comprises an emergency call mechanism that when activated transmits a wireless signal indicative of an emergency to the base station.

20. The portable remote device of claim 19, wherein the receiver receives an acknowledgement from the base station that the wireless signal indicative of an emergency was received and an acknowledgement message indicative of a call having been made to a third party is displayed on the portable remote device.

21. The portable remote device of claim 18, wherein the home/away sensor is activated by the individual when the home/away sensor is at least a predetermined distance from the base station.

22. The portable remote device of claim 18, wherein the portable remote device communicates with a mobile telephone.

23. The portable remote device of claim 18, wherein the portable remote device further includes a motion sensor and an emergency call mechanism that is activated after a predetermined amount of time if the motion sensor has not been activated within the predetermined amount of time.

24. A method for monitoring activity of an individual comprising:
- initiating a communication signal from a remote device to a base station for monitoring whether the remote device is within a distance of the base station; and
- receiving the communication signal at the base station;
- considering an individual present when the base station receives signals from the home/away sensor and another sensor indicates the presence of the individual in the dwelling; and
- considering the individual absent when the base station does not receive signals from the home/away sensor and another sensor indicates an exit of the individual from the dwelling.

25. The method of claim 24, wherein receiving the communication signal includes receiving information identifying a location of the remote device.

26. The method of claim 25, wherein the location of the remote device is identified by triangulation of a mobile telephone.

27. The method of claim 24, wherein the method includes initiating the communication signal using a short range wireless signal and translating the short range communication signal into a long range wireless signal.

28. The method of claim 27, wherein the long range wireless signal is sent to the base station using a mobile telephone.

29. The method of claim 28, wherein the short range communication signal is translated into a long range wireless signal if a distance between the remote device and the base station is greater than a distance between the remote device and the mobile telephone.

30. The method of claim 24, wherein the method includes initiating a confirmation signal from the base station to the remote device indicating the receipt of the communication signal; and
receiving the confirmation signal at the remote device.

31. The method of claim 30, wherein initiating the communication signal from the remote device includes sending the communication signal for a first predetermined amount of time at a first predefined time interval.

32. The method of claim 31, wherein initiating the communication signal from the remote device further includes sending the communication signal for a second predetermined amount of time at a second predefined interval when the confirmation signal from the base station is not received, and the second predetermined amount of time is less than the first predetermined amount of time.

33. The method of claim 32, wherein the remote device further includes an awaken mechanism where activating the awaken mechanism transmits a wireless signal indicative of a return of the remote device to within the distance of the base station and where the communication signal is sent at the first predetermined amount of time at the first predetermined time interval.

34. The method of claim 24, wherein the method further includes initiating a message-sent indication at the remote device indicating an emergency signal was sent to the base station;
initiating a message-received signal from the base station to the remote device indicating the receipt of the emergency signal;
receiving the message-received signal indication at the remote device;
initiating a message-relayed signal from the base station to the remote device indicating a call has been made to a third party; and
receiving the message-relayed signal indication at the remote device.

* * * * *